(12) United States Patent
Kim et al.

(10) Patent No.: US 10,004,727 B2
(45) Date of Patent: Jun. 26, 2018

(54) COMPOSITION FOR PREVENTING, ALLEVIATING OR TREATING METABOLIC DISEASES, CONTAINING AMODIAQUINE AS ACTIVE INGREDIENT

(71) Applicants: POSTECH ACADEMY—INDUSTRY FOUNDATION, Pohang-si (KR); NOVMETAPHARMA CO., LTD., Seoul (KR)

(72) Inventors: Kyong Tai Kim, Pohang-si (KR); Hoe Yune Jung, Gyeongju-si (KR)

(73) Assignees: POSTECH ACADEMY-INDUSTRY FOUNDATION, Pohang-si (KR); NOVMETAPHARMA CO., LTD., Seoul (KR)

( * ) Notice: Subject to any disclaimer, the term of this patent is extended or adjusted under 35 U.S.C. 154(b) by 0 days. days.

(21) Appl. No.: 15/551,310

(22) PCT Filed: Feb. 16, 2016

(86) PCT No.: PCT/KR2016/001571
§ 371 (c)(1),
(2) Date: Aug. 16, 2017

(87) PCT Pub. No.: WO2016/133352
PCT Pub. Date: Aug. 25, 2016

(65) Prior Publication Data
US 2018/0042917 A1 Feb. 15, 2018

(30) Foreign Application Priority Data
Feb. 16, 2015 (KR) ........................ 10-2015-0023442

(51) Int. Cl.
*A61K 31/4706* (2006.01)

(52) U.S. Cl.
CPC ............................... *A61K 31/4706* (2013.01)

(58) Field of Classification Search
None
See application file for complete search history.

(56) References Cited

U.S. PATENT DOCUMENTS

| | | |
|---|---|---|
| 8,440,695 B2 | 5/2013 | Kastan |
| 2009/0181976 A1 | 7/2009 | Buschmann et al. |
| 2009/0325975 A1* | 12/2009 | Buschmann ........... A61K 31/00 514/252.12 |
| 2014/0011839 A1 | 1/2014 | Obi |
| 2014/0162988 A1 | 6/2014 | Bannister et al. |
| 2015/0023930 A1 | 1/2015 | Rawat et al. |

OTHER PUBLICATIONS

Shimizu, S. et al., Metabolism-dependent Hepatotoxicity of Amodiaquine in Glutathione-depleted Mice. Archives of Toxicolog, 2009, vol. 83, pp. 701-707.

* cited by examiner

*Primary Examiner* — Brian J Davis
(74) *Attorney, Agent, or Firm* — Lex IP Meister, PLLC

(57) ABSTRACT

The present invention relates to a novel use of a composition containing, as an active ingredient, an amodiaquine compound or a pharmaceutically acceptable salt thereof and specifically, to a metabolic disease prevention, alleviation or treatment use of a composition containing, as an active ingredient, an amodiaquine compound or a pharmaceutically acceptable salt thereof, the composition activating both peroxisome proliferator-activated receptor-gamma (PPAR-γ) and peroxisome proliferator-activated receptor-alpha (PPAR-α).

3 Claims, 15 Drawing Sheets

COMPOSITION FOR PREVENTING, ALLEVIATING OR TREATING METABOLIC DISEASES, CONTAINING AMODIAQUINE AS ACTIVE INGREDIENT

TECHNICAL FIELD

The present invention relates to a composition for preventing, alleviating or treating a metabolic disease, which comprises amodiaquine which activates both of peroxisome proliferator-activated receptor-gamma (PPAR-γ) and peroxisome proliferator-activated receptor-alpha (PPAR-α) as an active ingredient.

BACKGROUND ART

Due to gradual westernization of Korean dietary culture, related metabolic diseases are increasing. One of the representative metabolic diseases is diabetes. Diabetes causes high blood glucose which is due to accumulation of glucose in the blood, not being used as energy, because a glucose regulatory hormone, insulin, secreted from pancreatic beta cells is not produced in the required amount in the body or does not properly act on cells, and has a symptom of glucose being detected in urine. Generally, diabetes is classified into insulin-dependent diabetes (type 1 diabetes) and non-insulin-dependent diabetes (type 2 diabetes) depending on whether insulin is essential for treatment. Type 2 diabetes is non-insulin-dependent diabetes developed due to an insufficient insulin action because of insulin resistance, or a relatively lack of insulin, and 90% of the total patients with diabetes have type 2 diabetes, which is also called adult diabetes because it generally occurs in people in their thirties.

When diabetes is long-term, since glucose in the body is not normally absorbed, resulting in abnormal glucose, lipid and protein metabolisms, various diabetic side effects such as hyperinsulinemia, neurologic complications, diabetic retinopathy (non-proliferative retinopathy, proliferative retinopathy, diabetic cataract), renal failure, sexual dysfunction, a dermal disease (allergy), high blood pressure, arteriosclerosis, cerebrovascular apoplexy (stroke), a cardiac disease (myocardial infarction, angina pectoris, heart attack), and gangrene occur. Therefore, while studies on glucose transport and metabolic processes and insulin signal transduction systems have been actively conducted domestically or globally to understand various reasons and etiological causes of type 2 diabetes and establish improvement plans, a drug that can be fundamentally used as a cure has not yet been developed.

Currently known drugs for type 2 diabetes may be broadly divided into four types, sulfonylurea-based drugs inducing insulin secretion, biguanide-based drugs exhibiting an effect of transferring glucose to muscle cells and inhibiting glucose synthesis in the liver, an α-glucosidase inhibitor that inhibits an enzyme for generating glucose in the small intestine, and thiazolidinedione (TZD)-based drugs that activate PPAR-γ involved in differentiation of adipocytes. However, such oral blood glucose-lowering agents involve various side effects such as hypoglycemia (sulfonylurea-based drug), nephrotoxicity (biguanide-based drug), lactic acidosis (biguanide-based drug), and diarrhea and stomachaches (α-glucosidase inhibitor).

Meanwhile, a peroxisome is one of the intracellular organelles that cause such abnormal metabolic function, plays an important role in oxygen, glucose, lipid and hormone metabolisms, and even widely affects regulation of cell proliferation and differentiation, and regulation of inflammatory mediators. In addition, a peroxisome affects formation of the cell membrane and mast cells as well as insulin sensitivity due to lipid metabolism and glucose metabolism, and affects oxidative stress, thereby playing an important role in aging and tumorigenesis. A peroxisome proliferator-activated receptor (PPAR) is one of the nuclear receptors that regulate gene expression by ligand binding, and various fatty acids act as endogenous ligands. Currently known PPARs are PPAR-α, PPAR-β/δ, and PPAR-γ.

PPAR-γ is most commonly found in adipose tissue, in addition to vascular endothelium, macrophages, and pancreatic β cells, and plays a critical role in regulating the differentiation of adipocytes and in systemic lipid homeostasis. An overall or partially-activated PPAR-γ compound is particularly effective in treating type 2 diabetes. However, obesity, dyslipidemia, a cardiovascular disease or fatty liver, which occurs as a side effect in PPAR-γ activation, becomes a problem.

PPAR-α is generally found in blood vessel walls, liver, heart, muscle, kidney, and brown adipose tissue, etc., prevents or delays arteriosclerosis together with an agonist, a fibrate, and exhibits an anti-obesity effect due to stimulation of fat oxidation.

Accordingly, to prevent, alleviate or treat various diseases regulated by a PPAR action, there is an increasing need to find a new compound that can effectively regulate PPAR activity.

For this reason, during research on compounds that have excellent antidiabetic activity and are capable of being safely applied, the inventors noticed amodiaquine.

There have been a variety of reports on amodiaquine, which is an anti-malarial compound, from studies on therapeutic agents for malaria. In addition, conventional patent technologies for amodiaquine include an anti-malarial mixed preparation for oral administration and a method of preparing the same (Korean Patent No. 10-0623322), and a piperazine derivative as an anti-malarial preparation (Korean Patent No. 10-1423785).

However, there are almost no studies and technologies with respect to amodiaquine for preventing, alleviating or treating a metabolic disease as a disease regulated by a PPAR action.

DISCLOSURE

Technical Problem

The present invention is directed to providing a novel use of a composition containing amodiaquine or a pharmaceutically acceptable salt thereof as an active ingredient, particularly, a novel use for preventing, alleviating or treating a metabolic disease in response to PPAR-γ and PPAR-α signals.

However, technical problems to be solved in the present invention are not limited to the above-described problems, and other problems which are not described herein will be fully understood by those of ordinary skill in the art from the following descriptions.

Technical Solution

The present invention provides a pharmaceutical composition for preventing or treating a metabolic disease, which contains amodiaquine represented by Formula 1 below or a pharmaceutically acceptable salt thereof as an active ingredient and activates both of PPAR-γ and PPAR-α.

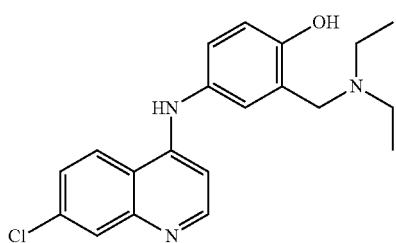

[Formula 1]

A daily dose of the composition may be 8 mg/kg to 20 mg/kg.

The metabolic disease may be one or more selected from the group consisting of diabetes, hyperglycemia, impaired glucose tolerance, obesity, dyslipidemia, arteriosclerosis, hypertension, insulin resistance syndrome, fatty liver, a cardiovascular disease, and syndrome X.

The dyslipidemia may be one or more selected from the group consisting of hyperlipidemia, hypertriglyceridemia, and hypercholesterolemia.

The metabolic disease may be type 2 diabetes in response to PPAR-γ activation.

The metabolic disease may be one or more selected from the group consisting of obesity, dyslipidemia, cardiovascular disease and fatty liver, which respond to PPAR-α activation, and occur as side effects in PPAR-γ activation.

According to an exemplary embodiment of the present invention, the present invention provides a health functional food composition for preventing or alleviating a metabolic disease, which contains amodiaquine represented by Formula 1 below or a pharmaceutically acceptable salt thereof as an active ingredient and activates both of PPAR-γ and PPAR-α.

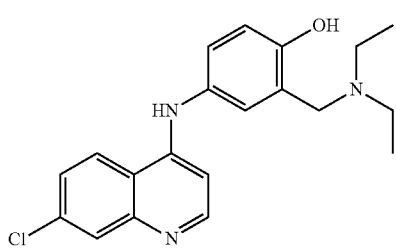

[Formula 1]

The metabolic disease may be one or more selected from the group consisting of diabetes, hyperglycemia, impaired glucose tolerance, obesity, dyslipidemia, arteriosclerosis, hypertension, insulin resistance syndrome, fatty liver, a cardiovascular disease, and syndrome X.

The dyslipidemia may be one or more selected from the group consisting of hyperlipidemia, hypertriglyceridemia, and hypercholesterolemia.

The metabolic disease may be type 2 diabetes in response to PPAR-γ activation.

The metabolic disease may be one or more selected from the group consisting of obesity, dyslipidemia, cardiovascular disease and fatty liver, which responds to PPAR-α activation and occurs as side effects in PPAR-γ activation.

Advantageous Effects

It was identified that a composition comprising amodiaquine or a pharmaceutically acceptable salt thereof as an active ingredient according to the present invention promotes the activity of PPAR-α and PPAR-γ. Particularly, because of effects of increasing glucose uptake, lowering and regulating blood glucose, reducing glycated hemoglobin (HbA1C), reducing a body weight, producing heat, preventing fatty liver and exhibiting anti-inflammation in adipose tissue, the composition of the present invention is expected to be useful to prevent, alleviate or treat PPAR-involved diseases, which are metabolic diseases such as diabetes (particularly, type 2 diabetes), hyperglycemia, impaired glucose tolerance, obesity, dyslipidemia, arteriosclerosis, hypertension, insulin resistance syndrome, fatty liver, a cardiovascular disease and syndrome X.

MODES OF THE INVENTION

Figure 1A:
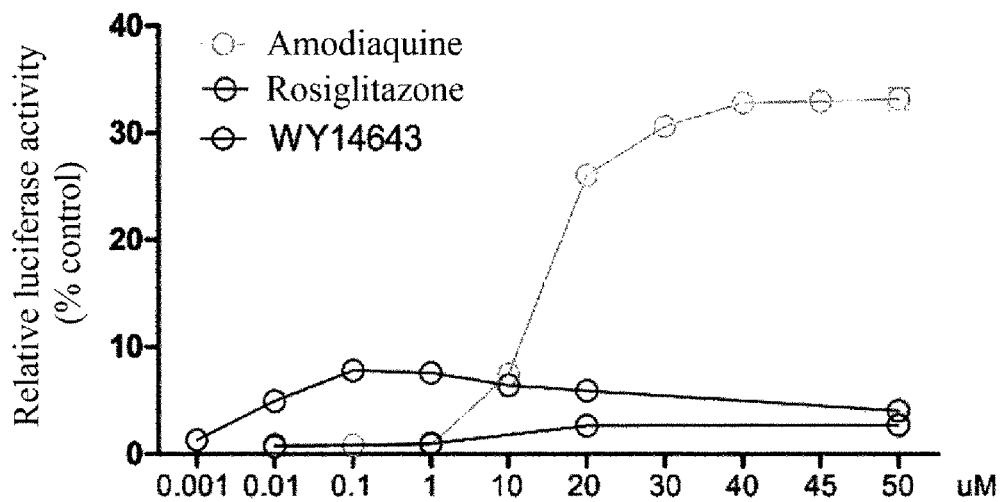
FIGS. 1A and 1B are graphs of detecting a PPAR-γ activating effect of amodiaquine.

The inventors developed a composition for preventing, alleviating or treating a metabolic disease, which comprises amodiaquine or a pharmaceutically acceptable salt thereof as an active ingredient, and activates both of PPAR-γ and PPAR-α, and thus the present invention was completed.

In an exemplary embodiment of the present invention, to examine whether amodiaquine serves as a double ligand for PPAR-γ and PPAR-α, the activity of PPAR-γ and PPAR-α were detected using vectors (see Example 1), and to examine whether an increase in the glucose uptake of amodiaquine affects a decrease in blood glucose, a test of evaluating glucose uptake in a mouse muscle cell line was performed (see Example 2). In addition, mice were examined to exhibit effects of lowering and regulating blood glucose, reducing glycated hemoglobin (HbA1C), reducing a body weight, producing heat and preventing fatty liver, due to amodiaquine (see Examples 3 to 8). Moreover, it was confirmed that the amodiaquine administration was able to promote degradation of fatty acids by regulating expression of target genes (ACOX, CPT-1 and mCAD) by PPAR-α activation in liver, muscle or adipose tissue (see Example 9), and it was confirmed that the amodiaquine administration was able to inhibit expression of target genes (TNFα, MCP-1 and iNOS) by anti-inflammatory responses in adipose tissue (see Example 10).

As a result, it was confirmed that the PPAR-γ and PPAR-α activation by amodiaquine treatment and a series of related responses are effective in inhibiting fat accumulation and regulating blood glucose.

Therefore, the present invention may use amodiaquine (4-[(7-chloroquinolin-4-yl)amino]-2-[(diethylamino) methyl]phenol) represented by Formula 1 below or a pharmaceutically acceptable salt thereof as a pharmaceutical composition for preventing or treating a metabolic disease to activate both of PPAR-γ and PPAR-α.

[Formula 1]

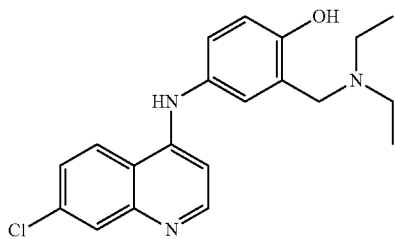

The metabolic disease may be one or more selected from the group consisting of diabetes, hyperglycemia, impaired glucose tolerance, obesity, dyslipidemia, arteriosclerosis, hypertension, insulin resistance syndrome, fatty liver, a cardiovascular disease, and syndrome X, but the present invention is not limited thereto.

In addition, the dyslipidemia may be one or more selected from the group consisting of hyperlipidemia, hypertriglyceridemia, and hypercholesterolemia, but the present invention is not limited thereto.

Here, a disease responding to PPAR-γ activation may be type 2 diabetes, and a disease responding to PPAR-α activation and occurring as a side effect in the PPAR-γ activation may be one or more selected from the group consisting of obesity, dyslipidemia, a cardiovascular disease and fatty liver, but the present invention is not limited thereto.

Accordingly, the composition may activate both of PPAR-γ and PPAR-α, and may be used to prevent or treat type 2 diabetes responding to PPAR-γ activation, and in this case, one or more selected from the group consisting of obesity, dyslipidemia, a cardiovascular disease and fatty liver, which respond to PPAR-α activation and occur as side effects in PPAR-γ activation, may be inhibited.

The term "treatment" used herein refers to all actions involved in alleviating or beneficially changing symptoms of a metabolic disease by administration of the pharmaceutical composition according to the present invention.

Accordingly, to prepare a pharmaceutical composition, a suitable carrier, excipient and diluent, which are conventionally used, may be further included. In addition, the composition may be formulated in an oral formulation such as powder, granules, tablets, capsules, suspensions, emulsions, syrups or aerosols, formulations for external use, suppositories and sterilized injections by a conventional method.

As the carriers, excipients and diluents that can be included in the composition, lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate and mineral oil may be used. The composition is prepared using a diluent or excipient such as a filler, a thickening agent, a binder, a wetting agent, a dispersant, or a surfactant, which is generally used.

The pharmaceutical composition of the present invention is administered at a pharmaceutically effective amount. In the present invention, the "pharmaceutically effective amount" refers to an amount sufficient to treat the disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in the medical field.

To improve a therapeutic effect, the pharmaceutical composition of the present invention is preferably administered simultaneously with, separately from and sequentially with a drug used in combination, or administered in a single dose or multiple doses. In consideration of all of the above-mentioned parameters, it is important to achieve the maximum effect with the minimum dose without a side effect, and such a dose may be easily determined by one or ordinary skill in the art. Specifically, the effective amount of the pharmaceutical composition of the present invention may vary depending on a patient's age, sex, conditions and a body weight, absorption of the active ingredient in the body, inactivation rate and excretion rate, a disease type or a drug used in combination.

The pharmaceutical composition of the present invention may be administered to a subject via various routes. Every administration route may be expected, and thus the pharmaceutical composition of the present invention may be administered, for example, orally, parenterally, nasally, intratracheally, by intraarterial injection, intravenous injection, subcutaneous injection, intramuscular injection or intraperitoneal injection. A daily dose of the pharmaceutical composition may be approximately 0.0001 mg/kg to 100 mg/kg, and preferably 8 mg/kg to 20 mg/kg, and the pharmaceutical composition may be administered in a single or multiple doses per day, but the present invention is not limited thereto. When the daily dose of the pharmaceutical composition is maintained at 8 mg/kg to 20 mg/kg, both of PPAR-γ and PPAR-α may be activated, and problems caused by toxicity are minimized.

The pharmaceutical composition of the present invention is determined by a type of drug, which is an active ingredient, as well as a variety of related parameters such as a disease to be treated, an administration route, a patient's age, sex and body weight, and the severity of the disease.

In another aspect of the present invention, the present invention provides a method of treating a metabolic disease, which comprises administering the pharmaceutical composition to a subject.

The "subject" used herein refers to a target with a disease to be treated, more specifically a human, or a mammal such as a non-human primate, a mouse, a rat, a dog, a cat, a horse or a cow.

Further, the present invention provides a use of the pharmaceutical composition to prevent or treat a metabolic disease.

Moreover, the present invention provides a health functional food composition for preventing or alleviating a metabolic disease, which comprises amodiaquine or a pharmaceutically acceptable salt thereof.

The term "alleviation" used herein refers to all types of actions that at least reduce parameters related to a condition to be treated, for example, a degree of a symptom. Here, the health functional food composition may be used together with or separately from a drug for treatment before or after the occurrence of a corresponding metabolic disease to prevent or improve the disease.

The term "health functional food composition" used herein comprises at least one of a carrier, a diluent, an excipient and an additive to be prepared in one form selected from the group consisting of tablets, pills, powders, granules, capsules and a liquid, and preferably a liquid. However, the present invention is not limited thereto.

Foods that can be added to the composition of the present invention may include various foods, powders, granules, tablets, capsules, syrups, beverages, gums, teas, vitamin complexes, and health functional foods. As an additive further included in the present invention, one or more types of ingredients selected from the group consisting of natural carbohydrates, sweeteners, nutrients, vitamins, minerals (electrolytes), flavoring agents (synthetic flavoring agents, natural flavoring agents, etc.), coloring agents, fillers, pectic acid and a salt thereof, alginic acid and a salt thereof, organic acids, protective colloid thickening agents, pH modifiers, stabilizers, preservatives, antioxidants, glycerin, alcohols, carbonating agents, and fruit flesh may be used. Examples of the above-mentioned natural carbohydrates include conventional sugars, for example, monosaccharides such as glucose, fructose, etc.; disaccharides such as maltose, sucrose, etc.; and polysaccharides such as dextrin, cyclodextrin, etc., and sugar alcohols such as xylitol, sorbitol, erythritol, etc. As the sweeteners, natural sweeteners [thaumatin, stevia extract (e.g., rebaudioside A, glycyrrhizin, etc.)] and synthetic sweeteners (saccharin, aspartame, etc.) may be advantageously used.

In addition to the above ingredients, the composition according to the present invention may contain a variety of nutrients, vitamins, minerals (electrolytes), flavoring agents including synthetic and natural flavoring agents, coloring agents and fillers (cheese, chocolate, etc.), pectic acid and a salt thereof, alginic acid and a salt thereof, an organic acid, protective colloid thickening agents, pH modifiers, stabilizers, preservatives, glycerin, alcohols, or carbonating agents used in carbonated beverages.

In addition, the composition according to the present invention may contain flesh for preparing natural fruit juices and vegetable juices. Such an ingredient may be used independently or in combination. Specific examples of the carriers, excipients, diluents and additives may include, but are not limited to, one or more selected from the group consisting of lactose, dextrose, sucrose, sorbitol, mannitol, erythritol, starch, acacia gum, calcium phosphate, alginate, gelatin, calcium phosphate, calcium silicate, microcrystalline cellulose, polyvinylpyrrolidone, cellulose, methyl cellulose, water, sugar syrup, methyl hydroxybenzoate, propyl hydroxybenzoate, talc, magnesium stearate, and mineral oil.

Hereinafter, exemplary examples will be provided to help in understanding of the present invention. However, the following examples are merely provided to facilitate understanding of the present invention, and the scope of the present invention is not limited to the following examples.

Preparation Example

Amodiaquine used in the following examples was purchased from Sigma-Aldrich.

EXAMPLES

Example 1. Detection of PPAR-γ or PPAR-α Activation by Amodiaquine

To examine whether amodiaquine serves as a ligand of PPAR-γ or PPAR-α, three types of vectors were used. An experiment was carried out by a known method (Cell, 68: 879-887, 1992) using a vector prepared by binding genes expressing a GAL4-DNA binding domain (DBD), which is a yeast transcription factor, and a human PPAR-γ-ligand binding domain (LBD) or PPAR-α-LBD to a SV40 promoter of a pZeo vector, a vector prepared by binding a gene in which a GAL4 gene-binding base sequence (5'-CTCG-GAGGACAGTACTCCG-3') is repeated 8 times to luciferase, which is a reporter gene, and a vector expressing β-galactosidase as a transfection control.

The activation of luciferase expression was detected 6 hours after BE(2)C cells were transformed with a GAL4-PPAR-γ-LBD plasmid or GAL4-PPAR-α-LBD plasmid, the GAL4-luciferase vector and the β-galactosidase vector, and growing amodiaquine-treated cells for 20 hours in a 5% $CO_2$ incubator. Here, an experimental group co-treated with amodiaquine at various concentrations (0.01 to 50 μM), a control treated with 0.3% dimethyl sulfoxide (DMSO), a positive control co-treated with a compound known as a PPAR-γ ligand, rosiglitazone (Sigma, USA), at various concentrations (0.001 to 50 μM), a positive control co-treated with a compound known as a PPAR-α ligand, WY-14,643 (Sigma, USA), at various concentrations (0.01 to 50 μM), and a positive control co-treated with a compound known as an amodiaquine derivative, chloroquine (7-chloro-4-(4-diethylamino-1-methylbutylamino)quinoline) (Sigma, USA), at various concentrations (0.001 to 50 μM) were compared. The test results were analyzed to see if there was significance between the experimental group and the controls according to a t-test, and it was shown that these groups showed a statistically significant difference.

Figure 1B:
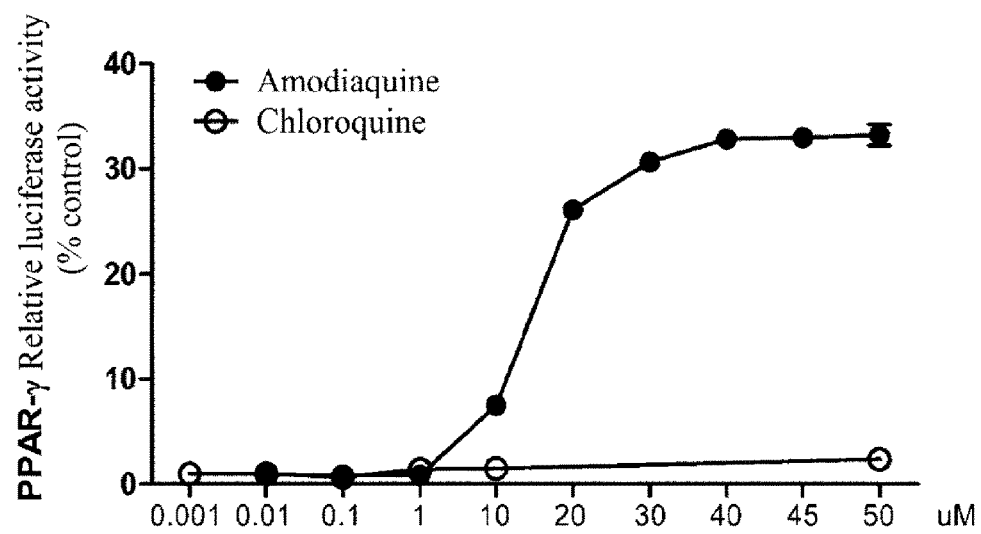
Figure 1C:
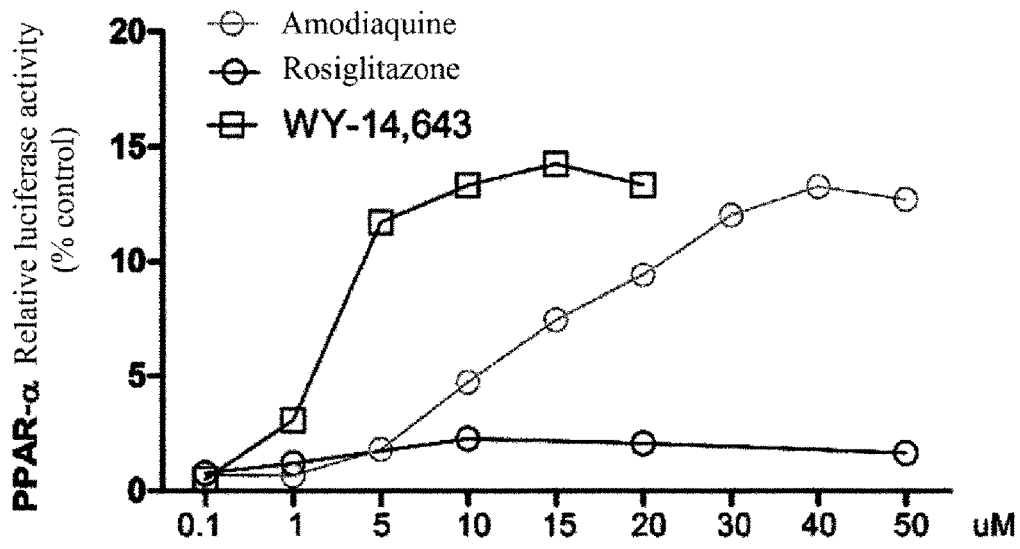
FIGS. 1C and 1D are graphs of detecting a PPAR-α activating effect.

As a result, as shown in FIGS. 1A and 1B, compared to the positive control treated with the compound known as a PPAR-γ ligand, rosiglitazone (Sigma, USA), it can be seen that the amodiaquine-treated group exhibit higher concentration-dependent PPAR-γ activity, the PPAR-γ activity was not shown in the positive control treated with the compound known as a PPAR-α ligand, WY-14,643, and the positive control treated with the compound known as an amodiaquine derivative, chloroquine. In addition, as shown in FIGS. 1C and 1D, similar to the positive controls treated with the compound known as a PPAR-α ligand, WY-14,643, the amodiaquine-treated group showed high concentration-dependent PPAR-α activity, but it can be confirmed that the positive control treated with the compound known as a PPAR-γ ligand, rosiglitazone, and the positive control treated with the compound known as an amodiaquine derivative, chloroquine, did not show the PPAR-α activity.

Therefore, it was confirmed that the amodiaquine treatment has an effect of stimulating the activity of both PPAR-γ and PPAR-α, and thus it can be seen that amodiaquine can be used to prevent or treat a metabolic disease such as type 2 diabetes, which is a PPAR-γ-involved disease, and to prevent or treat a metabolic disease such as obesity, dyslipidemia, a cardiovascular disease or fatty liver, which is regulated by PPAR-α signals.

Figure 1D:
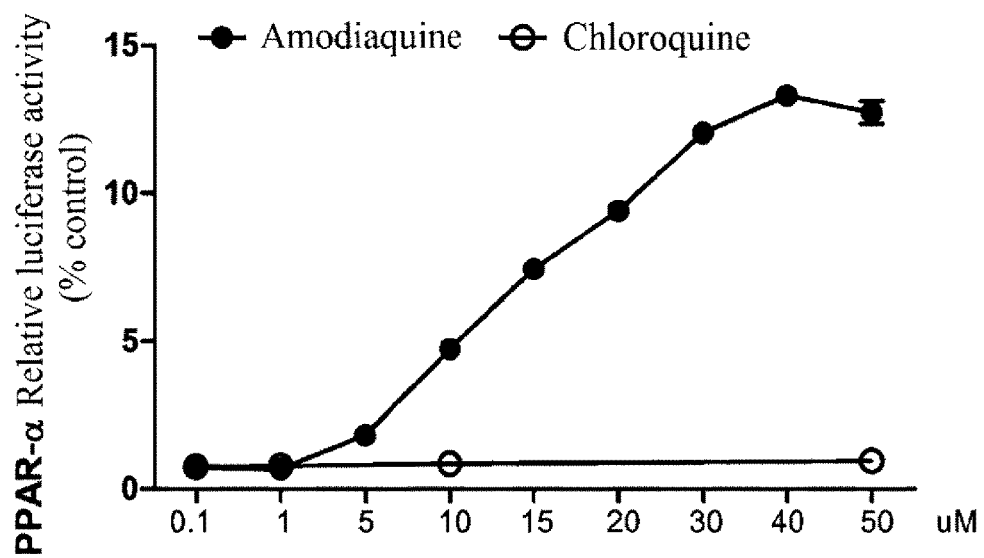

From the results shown in FIGS. 1B and 1D, it can also be seen that amodiaquine promotes the activity of both PPAR-γ and PPAR-α because of the structural characteristic in which a benzene ring and a hydroxyl group are substituted, but the amodiaquine derivative does not promote the same activity.

Example 2. Detection of Glucose Uptake of C2C12 Myotube Cells

Phosphorylation of insulin receptors occurs due to signal transduction by insulin in muscle, adipose or liver cells, and therefore when various proteins located downstream are phosphorylated, glucose uptake increases resulting in reduced blood glucose. A glucose uptake evaluation test was performed to identify whether amodiaquine is effective in diabetes. C2C12 myoblasts, which are muscle cells, were cultured in 10% bovine serum albumin (BSA)-containing DMEM. When the cell density reached approximately 80 to 90%, the medium was replaced with fresh 2% horse serum-containing DMEM, and cell differentiation of the C2C12 myoblasts to myotubes was induced to make them completely differentiated, followed by carrying out an experiment. The completely differentiated C2C12 myotube cells were treated with a well-mixed mixture of either of 10 and 30 µM amodiaquine, 0.1% DMSO, and 50 µM rosiglitazone (Sigma, USA), which is a compound known as a positive control for glucose uptake in 0.5% BSA-containing DMEM for 24 hours. After 24 hours of the treatment, the medium was removed, the cells were washed with 3 ml of KRP (0.1% BSA+5 mM glucose) buffer on a plate maintained at 37° C. to remove remaining specimens. Washing was repeated three times every twenty minutes. Subsequently, 1 ml of KRP buffer was injected, a solution (0.2 mM, 0.2 µCi) prepared by dissolving unlabeled 2-DOG and [$^3$H]2-DOG (Amersham Pharmacia) in KRP buffer was added at 37° C. to allow treatment for exactly 10 minutes. The resulting cells were washed with 3 ml of cold phosphate buffered saline (PBS) to stop a glucose uptake reaction, further washed twice with PBS, air-dried for approximately 1 hour, and lyzed with 1 ml of 0.1% SDS by pipetting, and then 300 µl of the lysate was obtained to detect radioactivity using a liquid scintillation counter (Perkin Elmer, USA).

Figure 2:
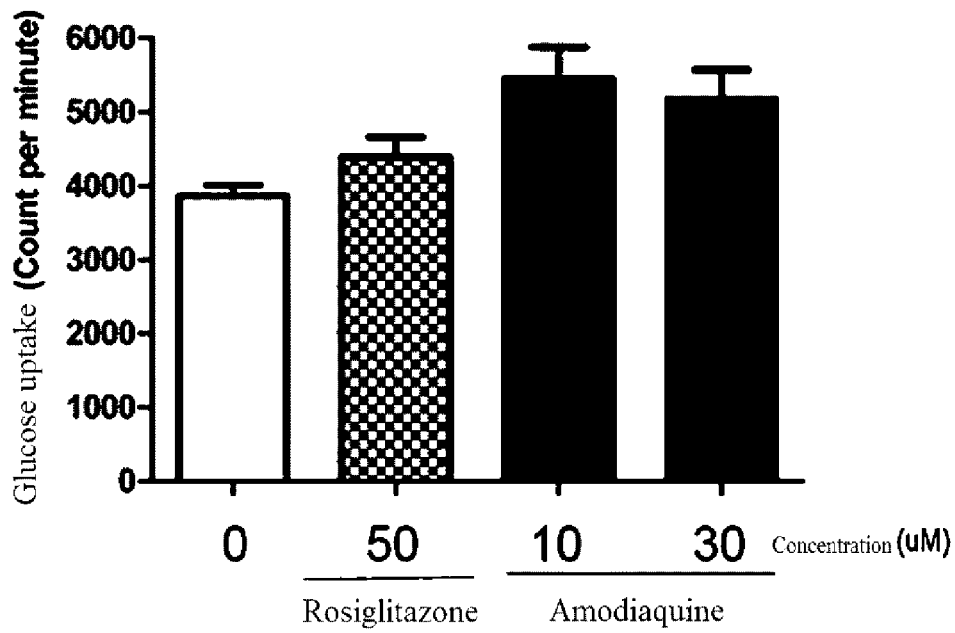
FIG. 2 is a graph of detecting the uptake of a glucose derivative when a C2C12 myotube cell line, which refers to mouse-derived muscle cells, was treated with amodiaquine for 24 hours.

As a result, as shown in FIG. 2, it was confirmed that the glucose uptake in the amodiaquine-treated groups is further increased than that in the rosiglitazone-treated group, which are the positive controls.

Therefore, it can be seen that amodiaquine, which is the representative target protein of a diabetes drug, increases PPAR-γ activity in cells, and promotes glucose uptake into the muscle cells.

Example 3. Detection of Effects of Amodiaquine on Lowering and Regulation of Blood Glucose in Mice 3-1. Administration of Amodiaquine and Negative Control Following one-week acclimation, 5-week-old KKAy mice purchased from Saeronbio Inc. were divided into two groups of 5.

The first group was set as a negative control by administering PBS, and the second group was treated by daily oral administration of amodiaquine at 18 mg/kg for 6 weeks.

3-2. Detection of Effects of Drop in Fasting Blood Glucose and Blood Glucose Regulation in Mice Fasting blood glucose was measured for 6 weeks from whole blood taken from the caudal vein of each mouse 1, 2, 5 and 6 weeks after 12-hour fasting. For blood glucose measurement, a blood glucose strip (Green Cross, Gyeonggi-do, Korea) was used. The test results were analyzed to see if there was significance between the experimental group and the control group according to a t-test, and it was shown that these groups showed a statistically significant difference ($*p<0.05$, $**p<0.005$). In addition, to identify the blood glucose regulation effect, 2 g/kg of glucose was intraperitoneally injected into the mice of the control and experimental group after 16-hour fasting, and the level of blood glucose was measured every 30 minutes for 2 hours. For measurement of the blood glucose concentration, an intraperitoneal glucose tolerance test (IPGTT) was used. The test results were analyzed to see if there was significance between the experimental group and the control group according to a t-test, and it was shown that these groups showed a statistically significant difference ($*p<0.05$, $**p<0.005$).

Figure 3A:
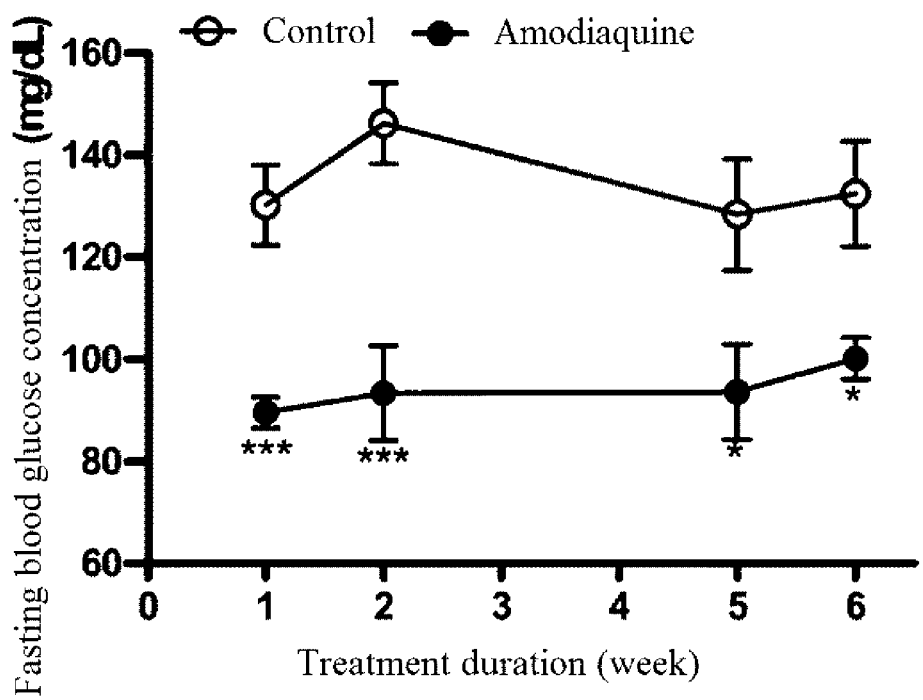
FIG. 3A is a graph showing an effect of amodiaquine uptake on a fasting blood glucose concentration of a mouse.
Figure 3B:
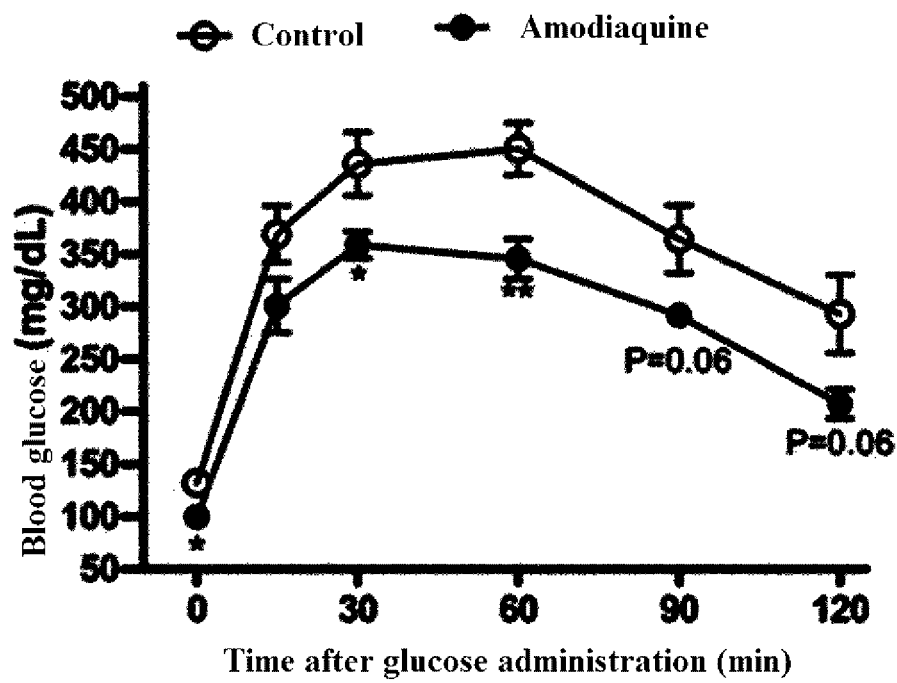
FIG. 3B is a graph showing a result of an intraperitoneal glucose tolerance test (IPGTT) showing an effect of amodiaquine uptake on a change in blood glucose over time after glucose administration to a mouse.

As a result, as shown in FIG. 3A, it was confirmed that fasting blood glucose was significantly decreased in the amodiaquine-administered mice relative to the control. Moreover, as shown in FIG. 3B, it was confirmed that 2 hours after glucose was administered, the blood glucose was more rapidly reduced in the amodiaquine-administered group relative to the control. Specifically, the fasting blood glucose concentrations were 132.4 mg/dl in the control and 100.2 mg/dl in the amodiaquine-administered group, and 2 hours after glucose loading, the blood glucose concentrations were 293.2 mg/dl in the control and 207 mg/dl in the amodiaquine-administered group.

Accordingly, since amodiaquine has an excellent effect of reducing blood glucose concentration, it can be seen that a pharmaceutical composition comprising amodiaquine as an active ingredient can be useful to prevent or treat diabetes, and due to the fasting blood glucose-reducing effect of amodiaquine, it can also be seen that a pharmaceutical composition comprising amodiaquine as an active ingredient can be useful to be a drug for preventing or treating insulin-resistant type 2 diabetes.

Example 4. Effect of Amodiaquine on HbA1C Content

Some of the glucose distributed in the blood is tightly bound with red blood cells, which is called glycated hemoglobin (HbA1C). To investigate blood glucose regulation, not only a glycated hemoglobin level but also a blood glucose concentration is detected. It is because a 1% decrease in glycated hemoglobin leads to a 20% decrease or more in complications due to diabetes. In this example, a change in glycated hemoglobin content in mice by amodiaquine intake was examined.

4-1. Administration of Amodiaquine and Negative Control

To detect a change in glycated hemoglobin content in mice by amodiaquine, after 1-week acclimation, 5-week-old KKAy mice were purchased from Saeronbio Inc. were divided into two groups of 5. Like in Example 3, the first group of mice were set as a control by administering PBS, and the second group was treated by daily oral administration of amodiaquine at 18 mg/kg for 6 weeks using a 1 ml syringe.

4-2. Measurement of Glycated Hemoglobin Contents in Mice

To detect an effect of amodiaquine on reducing glycated hemoglobin content, whole blood was taken from the caudal vein of each mouse in the control and experimental group, injected into an easy A1c cartridge, and then assessed using an easy A1c analyzer (Asan Pharmaceutical Co., Ltd., Seoul, Korea). An independent group t-test was performed on the experimental group and the control to identify significance in the test results, and a statistically significant difference was shown (**p<0.005).

Figure 4:
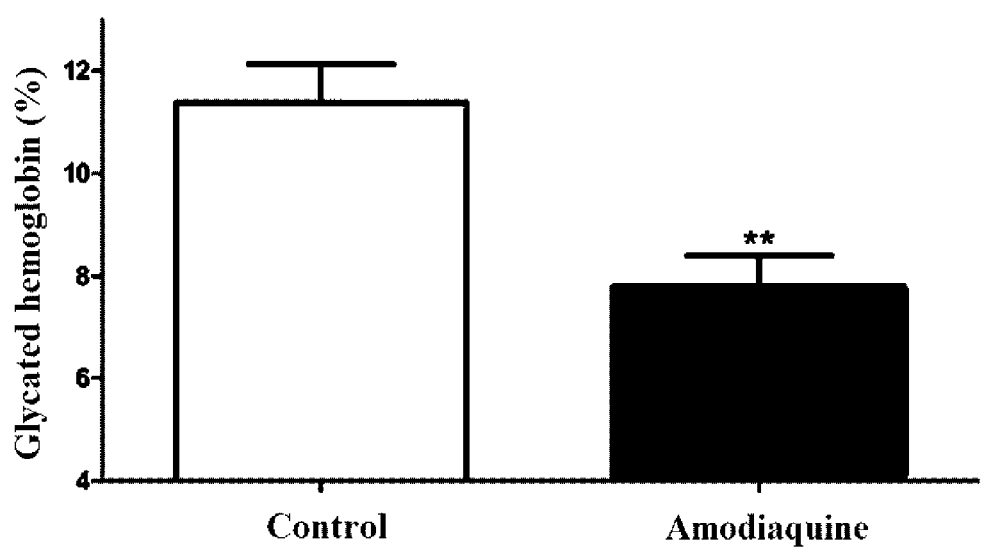
FIG. 4 is a graph showing an effect of amodiaquine uptake on a glycated hemoglobin level of a mouse.

As a result, as shown in FIG. 4, production of glycated hemoglobin was inhibited to almost 69% in the amodiaquine-administered mice, relative to the control mice.

Therefore, it can be seen that amodiaquine has an effect of reducing glycated hemoglobin content.

Example 5. Detection of Decrease in Body Weight Due to Amodiaquine

5-1. Design of Experimental Animals and Formulations of Experimental Diets

To detect a decrease in body weight of a mouse by amodiaquine, 7-week-old male C57BL/6 mice (Charles River Laboratories, Tokyo, Japan) were purchased and raised under predetermined conditions (temperature: 22±2° C., relative humidity: 55±10%, light/dark cycle: 12 hours). The mice were divided into groups of 7, freely fed water and diets in a cage, and then acclimated for 1 week before an experiment.

After acclimatization, the mice were divided into 7 groups, and fed diets with administration of amodiaquine and positive controls (WY-14,643, rosiglitazone) for the durations shown in Table 1.

TABLE 1

| Group | Type of diet | Amodiaquine (mg/kg) | WY-14,643 (mg/kg) | Rosiglitazone (mg/kg) | Duration |
|---|---|---|---|---|---|
| Normal control | LFD | — | — | — | Substance administration for 14 weeks |
| High fat control | HFD | — | — | — | |
| Positive control (for prevention) | HFD | — | 50 | — | |
| Amodiaquine group | HFD | 20 | — | — | |
| High fat control | HFD | — | — | — | Substance administration for 7 weeks after 15-week induction with HFD |
| Positive control (for treatment) | HFD | — | — | 50 | |
| Amodiaquine group | HFD | 20 | — | — | |

LFD (10% kcal as fat; D12450B, Research Diets Inc.)
HFD (60% kcal as fat; D12492, Research Diets Inc.)

5-2. Detection of Change in Body Weight in Mice

For examination of a change in body weight, body weights of normal diet-fed mice, high fat-induced obesity mice fed a high fat diet and high fat-induced obesity mice fed a high fat diet with amodiaquine and positive controls (WY-14,643 and rosiglitazone) were measured using an electron measurer (Dragon 204/S, Mettler Toledo, USA) for 21 weeks on the basis of 10 am once a week. An average body weight was calculated by dividing the sum of weights of 7 mice per group by the number of mice. An independent group t-test was performed on the high fat-induced obesity control, the amodiaquine group and the positive controls (WY-14,643 and rosiglitazone) to identify whether the experimental results have significance, and a statistically significant difference was shown (*P<0.05, P<0.005, *P<0.0005).

Figure 5A:
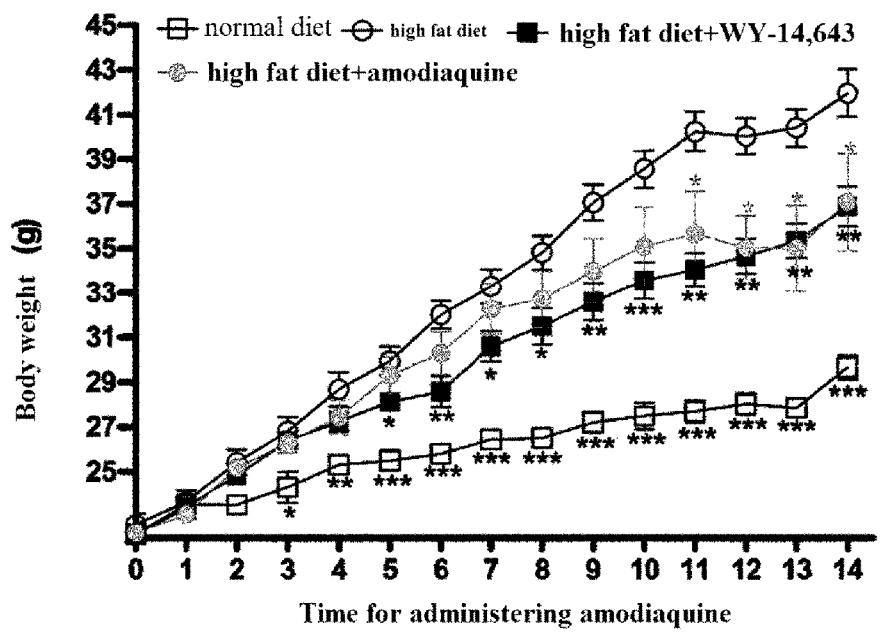
FIG. 5A is a graph showing an obesity inhibitory phenomenon of a mouse when high fat diet-induced obesity mice were fed a high fat diet with simultaneous administration of amodiaquine.
Figure 5B:
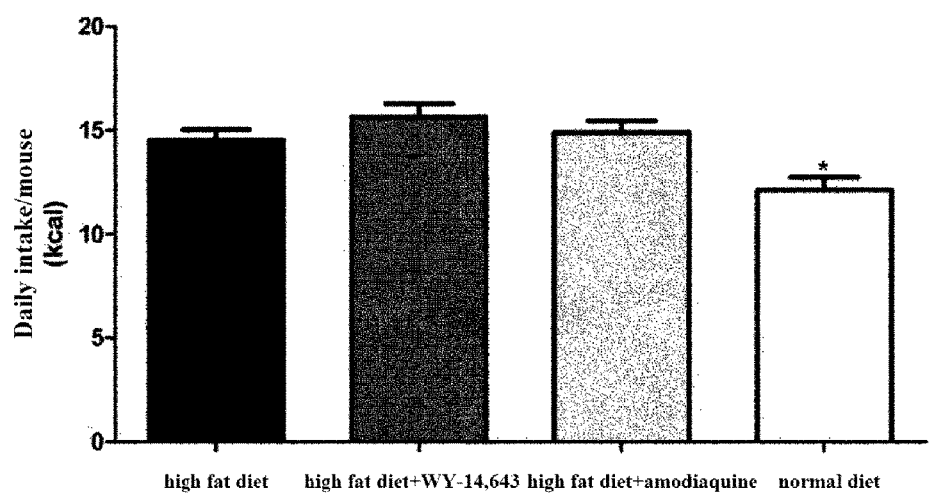
FIG. 5B is a graph showing a daily average feeding uptake of a mouse.
Figure 5C:
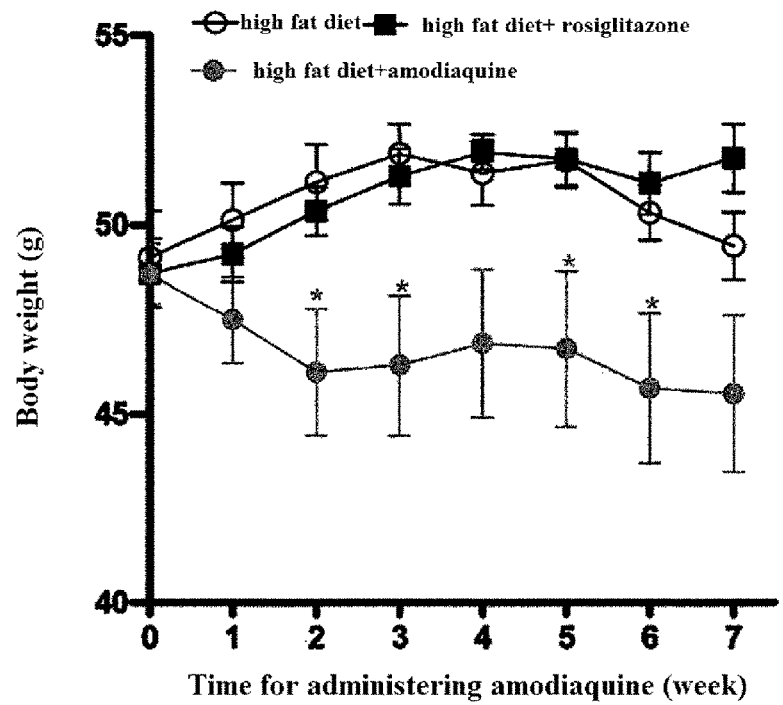
FIG. 5C is a graph showing an obesity-treated phenomenon by long term amodiaquine administration to high fat diet-induced obesity mice (20 weeks)

As shown in FIG. 5A, it can be observed that the body weight of the high fat-induced obesity mouse in the amodiaquine-administered group was significantly lower than that of the high fat-induced obesity mouse, and similar to that of the positive control (WY-14,643). As shown in FIG. 5C, it can also be observed that the body weight of the mouse in which obesity was induced with a high fat diet and then amodiaquine was administered was significantly lower than that of the high fat-induced obesity mouse. On the other hand, it can be confirmed that the body weight of the mouse treated with the positive control (rosiglitazone), which is a PPAR-γ agonist, was similar to or higher than that of the high fat-induced obesity mouse.

5-3. Measurement of Feed Intake of High Fat-Induced Obesity Mouse

Figure 5D:
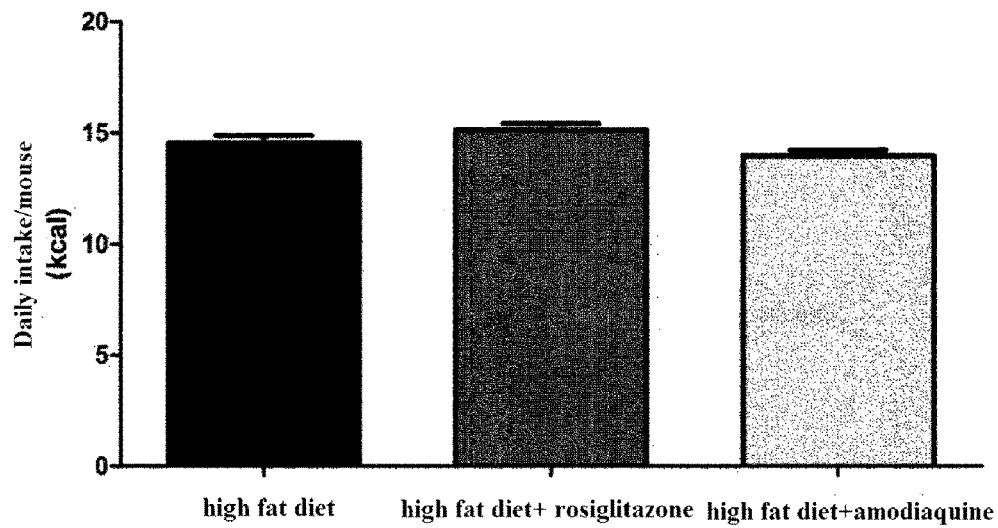
FIG. 5D is a graph showing a daily average feeding uptake of each mouse.

Feed intakes were measured for a mouse fed a normal diet, a high fat-induced obesity mouse fed a high fat diet and a high fat-induced obesity mouse fed a high fat diet with amodiaquine and the positive controls (WY-14,643 and rosiglitazone) on the basis of every 11 a.m. An average feed intake was obtained by dividing the feed intakes of 7 mice per group by 7. Every feed intake was converted into kcal. Consequently, as shown in FIGS. 5B and 5D, it can be observed that there was no difference between the feed intake of a high fat-induced obesity mouse treated with amodiaquine and the positive controls (WY-14,643 and rosiglitazone) and the feed intake of the high fat-induced obesity mouse.

The result shows that amodiaquine has an effect of reducing the body weight of a mouse regardless of feed intake, and thus can be used as an anti-obesity medicine.

Example 6. Measurement of Effect of Amodiaquine on Thermal Production

Adipose cells were divided into white adipose cells acting on lipid accumulation, and brown adipose cells acting on thermal production even with a very small amount. The brown adipose cells act on diet-inducible thermal production to make a body keep warm after feeding, and when a temperature is reduced, activity is increased and thus the body temperature is maintained due to thermal production. Due to poor functioning of the brown adipose cells, when an ob/ob mouse, which is an obesity test model and a genetic obesity animal, was exposed to a low temperature of 4° C., the ob/ob mouse was gradually decreased in body temperature and died after approximately 4 hours. When the brown adipose cells malfunction, because there is little energy lost as heat at a normal temperature, excessive energy is accumulated and thus obesity is highly likely to occur. Accordingly, in this example, a thermal production capability of the high fat-induced obesity mouse due to amodiaquine administration was examined.

6-1. Measurement of Thermal Production Capability of High Fat-Induced Mouse

To measure a thermal production capability with respect to mice fed a high fat diet for 14 weeks among the experimental animals designed in Example 5, a 4° C. cold test was performed (Spiegelman B. M. et al., Cell 92: 829-839, 1998). Hereinafter, the measurement method will be described in detail. A body temperature of mice in the high fat-induced obesity mouse groups was measured before being exposed to 4° C. and recorded as a test start temperature, and then the mice were exposed to 4° C. for up to 6 hours, followed by measuring a body temperature. The body temperature was measured using a rectal thermometer for a mouse (testo 925, Germany) A thermal production value indicated a temperature measured every hour. The test results were analyzed to see if there was significance between the experimental group and the control group according to a t-test, and it was shown that these groups showed a statistically significant difference (*$p<0.05$, ***$p<0.0005$).

Figure 6:
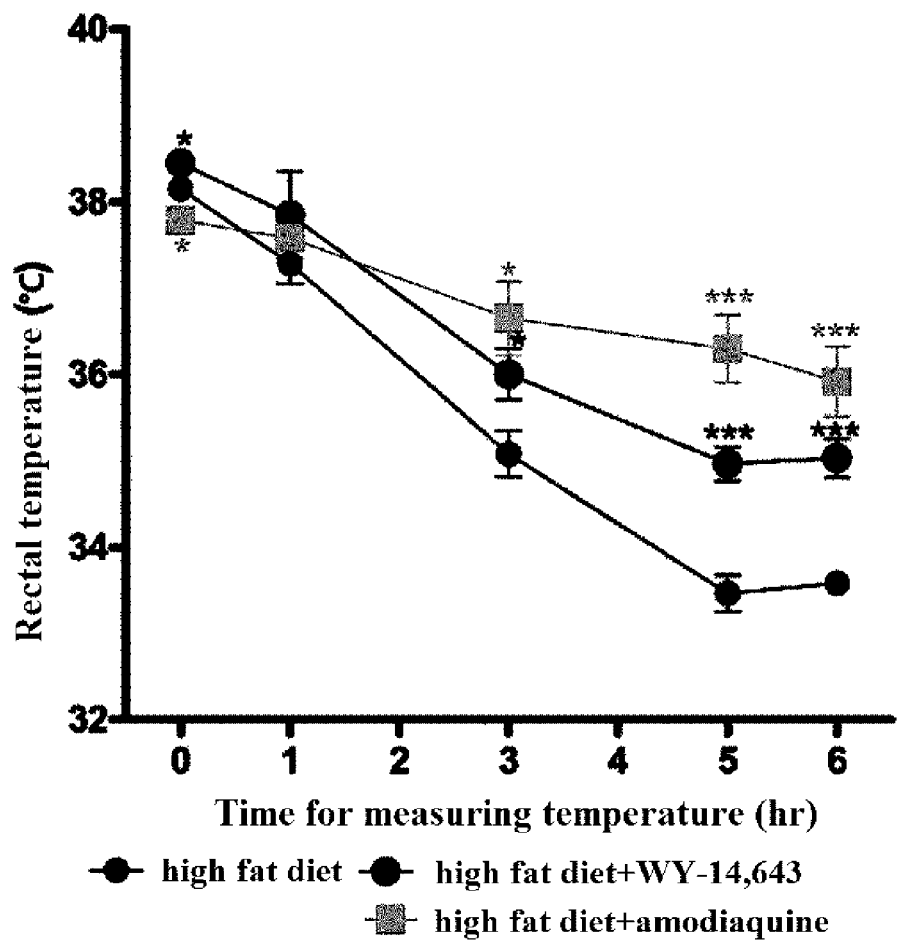
FIG. 6 is a graph showing thermal production of a high fat diet-induced obesity mouse when exposed to low temperatures, due to amodiaquine uptake.

As shown in FIG. 6, it was identified that the high fat obesity-induced mouse of the amodiaquine-administered group was less decreased in body temperature than the high fat obesity-induced mouse, and exhibited an excellent thermal production effect.

Accordingly, since the amodiaquine according to the present invention increased the thermal production activity of the high fat-induced obesity mouse to generate high energy as heat, it can be seen that amodiaquine has an effect of lowering the possibility of obesity.

Example 7. Measurement of Effect of Amodiaquine on Blood Glucose Regulation in Mice In this example, to measure a blood glucose regulation effect with respect to the experimental animals designed in Example 5, an IPGTT and an IPITT were performed.

7-1. Measurement of Oral Glucose Tolerance Test for Mice

After 16-hour fasting, 2 g/kg of glucose was orally administered to each animal in the controls and experimental group, and a blood glucose concentration was measured every 30 minutes for 2 hours. For measurement of the blood glucose concentration, an OGTT was used. The experimental results were analyzed to see if there was significance between the high fat-induced obesity mice control, the high fat-induced obesity mice treated with amodiaquine and the high fat-induced obesity mice treated with the positive control (WY-14,643), and the normal diet-fed mice according to a t-test, and it was shown that these groups showed a statistically significant difference (*$p<0.05$, $p<0.005$, *$p<0.0005$).

Figure 7A:
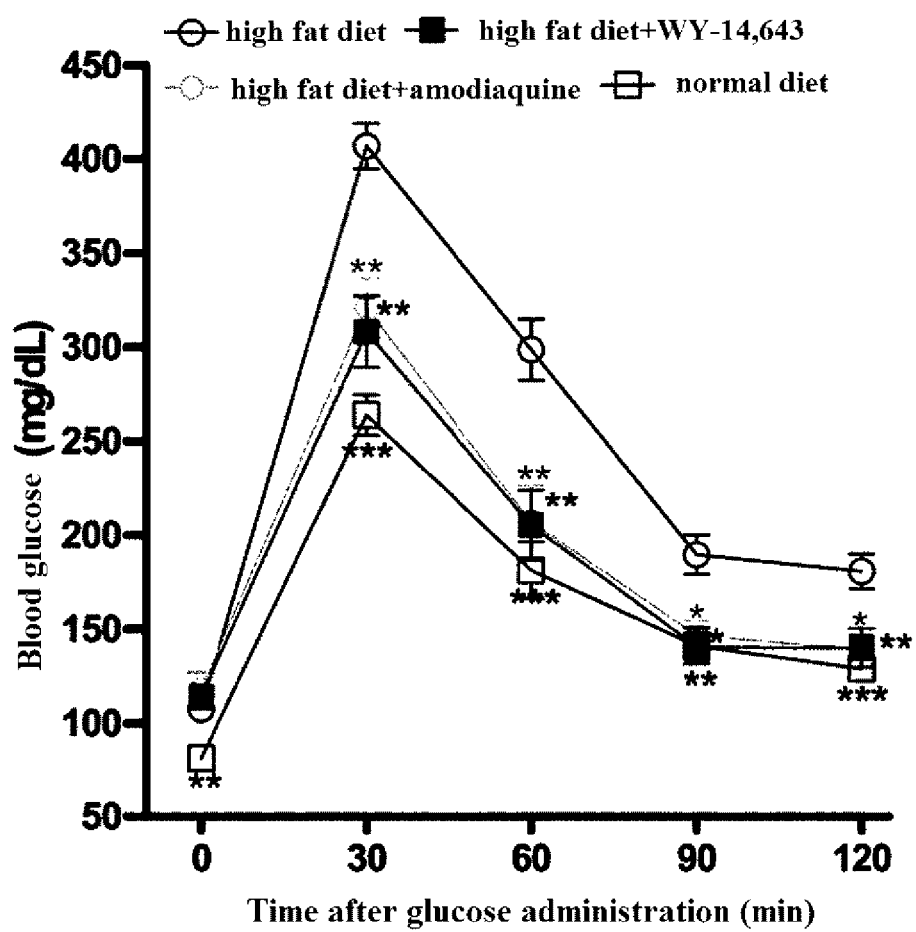
FIG. 7A is a graph showing a result of an oral glucose tolerance test (OGTT) showing an effect on a change in blood glucose over time when glucose is administered to mice which have simultaneously taken in amodiaquine and a high fat diet.

As a result, as shown in FIG. 7A, relative to high fat-induced obesity mice as a control, 2 hours after glucose was administered to the amodiaquine-administered group, it was confirmed that blood glucose was rapidly reduced. Specifically, 2 hours after the glucose loading, the blood glucose concentration was 180.5 mg/dl in the high fat-induced obesity mouse control, and the blood glucose concentration was 139.1 mg/dl in the amodiaquine-administered group.

Accordingly, since amodiaquine exhibits an excellent effect of reducing blood glucose concentration, it can be seen that a pharmaceutical composition comprising amodiaquine as an active ingredient can be useful as a drug for preventing and treating insulin-resistant type 2 diabetes.

7-2. Measurement of IPITT for Mice

After 16-hour fasting, 0.5 U/kg of insulin was intraperitoneally administered to each animal in the controls and the experimental group, and a blood glucose concentration was measured every 30 minutes for 2 hours. For measurement of the blood glucose concentration, an IPITT was used. The experimental results were analyzed to see if there was significance between the high fat-induced obesity mouse control, the high fat-induced obesity mice treated with amodiaquine, the high fat-induced obesity mice treated with positive controls (WY-14,643 and rosiglitazone) and the normal diet-fed mice according to a t-test, and it was shown that these groups showed a statistically significant difference (*$p<0.05$, $p<0.005$, *$p<0.0005$).

Figure 7B:
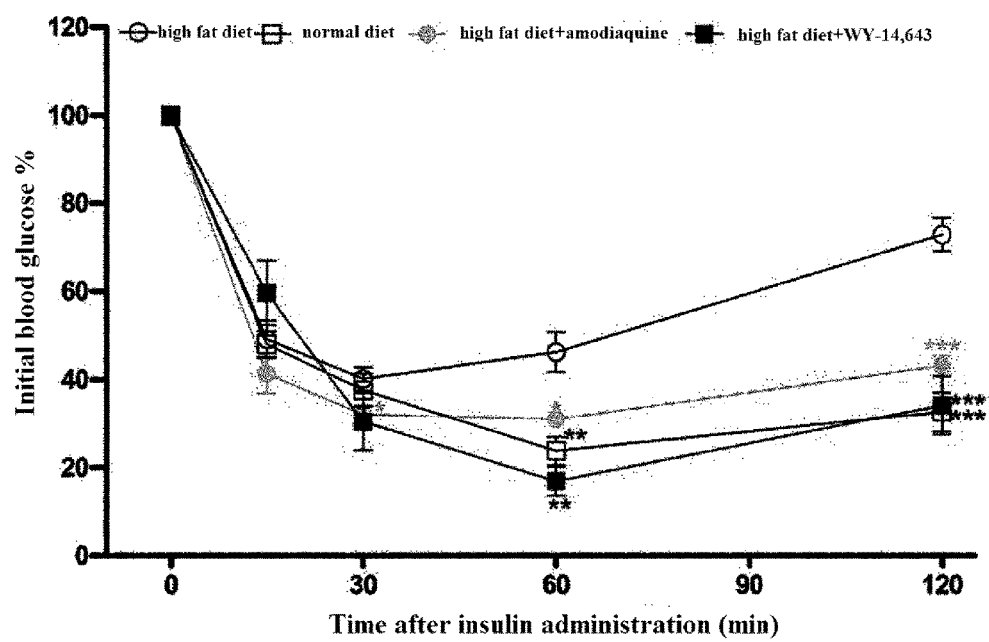
FIG. 7B is a graph showing an intraperitoneal insulin tolerance test (IPITT) showing a change in blood glucose concentration over time after insulin is injected into mice which have simultaneously taken in amodiaquine and a high fat diet.
Figure 7C:
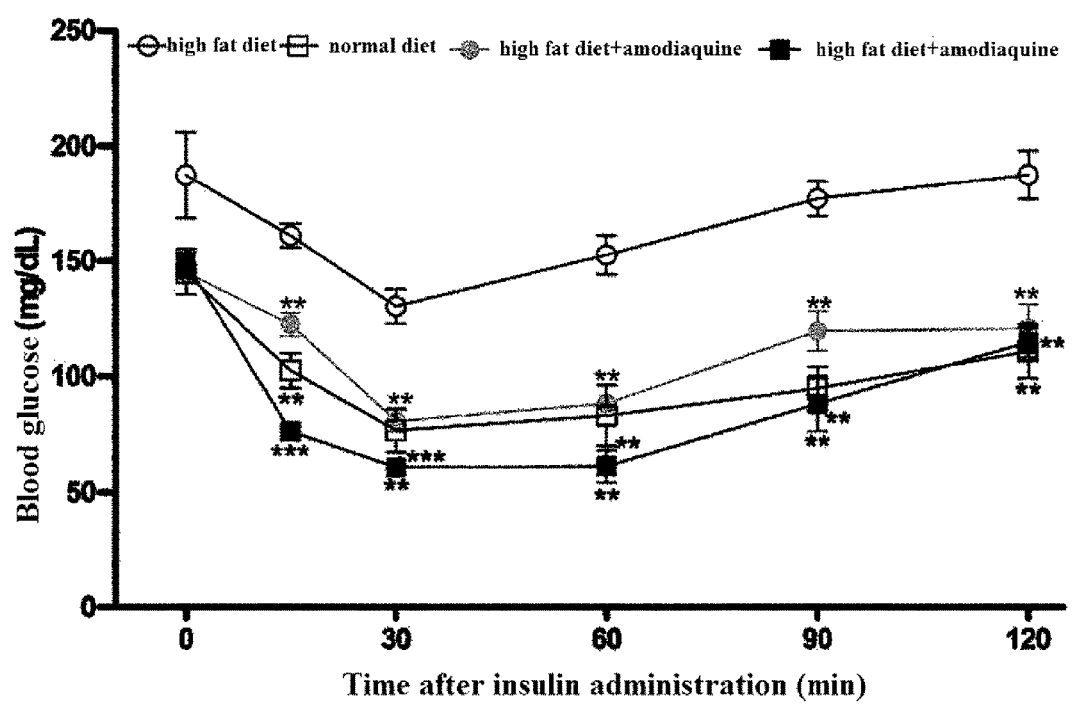
FIG. 7C is a graph showing an IPITT identifying a change in blood glucose concentration over time after insulin was injected after amodiaquine was administered to a mouse fed a long-term (20 weeks) high fat diet.

Consequently, as shown in FIG. 7B, when insulin was administered to a high fat-induced obesity mouse control and an experimental group to measure insulin resistance, the blood glucose was detected at the lowest level in all groups at 30 minutes, and then gradually increased. In the high fat-induced obesity mouse control, a blood glucose concentration was increased to a fasting blood glucose concentration at 120 minutes, and in the normal diet-fed group, the positive control (WY-14,643), and the amodiaquine-administered group, after 2 hours, a blood glucose concentration was maintained lower than the fasting blood glucose concentration. In addition, as shown in FIG. 7c, insulin was administered to the insulin-resistant obesity mouse control induced by a high fat diet and the experimental group, and initial blood glucose was indicated in percentage (%). According to the measurement of insulin resistance, in the high fat-induced obesity mice and the amodiaquine-administered group, the insulin resistance was measured at the lowest level at 30 minutes, and then gradually increased. In the positive control (rosiglitazone) and the normal diet-fed group, the blood glucose concentration was at the lowest level at 60 minutes, and then gradually increased. In the high fat-induced obesity mouse control, the blood glucose concentration at 120 minutes was increased to approximately 70% of the initial blood glucose, and in the normal diet-fed group, the positive control (rosiglitazone), and the amodiaquine-administered group, the blood glucose after 2 hours was maintained at approximately 40 to 45% of the initial blood glucose.

Accordingly, since the intake of amodiaquine increases insulin sensitivity, it can be seen that amodiaquine can be useful as a drug for preventing or treating insulin-resistant type 2 diabetes.

Example 8. Measurement of Effect of Amodiaquine on Preventing Fatty Liver

Fatty liver can be caused by a nutritional imbalance related to high calorie and high fat diets and the intake of simple sugar, other than alcoholic fatty liver occurring due to excessive intake of alcohol. Particularly, the continuous intake of a high calorie or high fat diet causes a lipid metabolic disorder between lipogenesis and lipolysis in the liver, resulting in fatty liver (Fromenty B. et al., Mitochondrion 6:1-28, 2006).

In this example, an effect on fatty liver induction by treatment with amodiaquine was examined.

8-1. Tissue Collection from High Fat-Induced Obesity Mouse Group

Among the experimental animals designed in Example 5, mice in the high fat-induced obesity mouse group fed a high fat diet for 14 weeks were sacrificed by cervical spine dislocation, fixed on a dissection stand, and subjected to abdominal dissection with a scalpel to extract the liver. The extracted liver tissue was fixed in a 10% formalin solution to prevent contracted deformation. After the fixed tissue was washed with running water after 24 hours, general tissue dehydration, clearing and impregnation were performed using an automatic tissue processor (6460B, Sakura, Japan) for 14 hours, and manufacture of paraffin blocks and cooling were performed using an automated embedding device (Tissue-Tex, Japan). The manufactured paraffin blocks were continuously sliced to a thickness of 4 to 5 µm in a vertical direction of the tissue using a rotary microtome 2040 (Japan), and attached to slides after processing using a water bath and a slide warming table.

8-2. Observation of Effect of Amodiaquine on Preventing Fatty Liver

The thin tissue section was stained with hematoxylin, an excessively-stained part was washed with running tap water, and then the resulting section was dipped in 1% HCl and a 70% A/C solution 3 to 5 times to stain the nuclei blue. Subsequently, the section was sufficiently washed for approximately 5 to 10 minutes, subjected to cytoplasmic counter staining to make the nuclei clear, and washed with running water for 15 seconds to remove an excessive eosin solution, followed by tissue dehydration and clearing. Each liver tissue was observed using an optical microscope (BX50, Olympus, Japan), and an image of tissue in each group was taken using a CCD camera (PM-C35DX, Olympus, Japan) equipped with a microscope.

Figure 8:
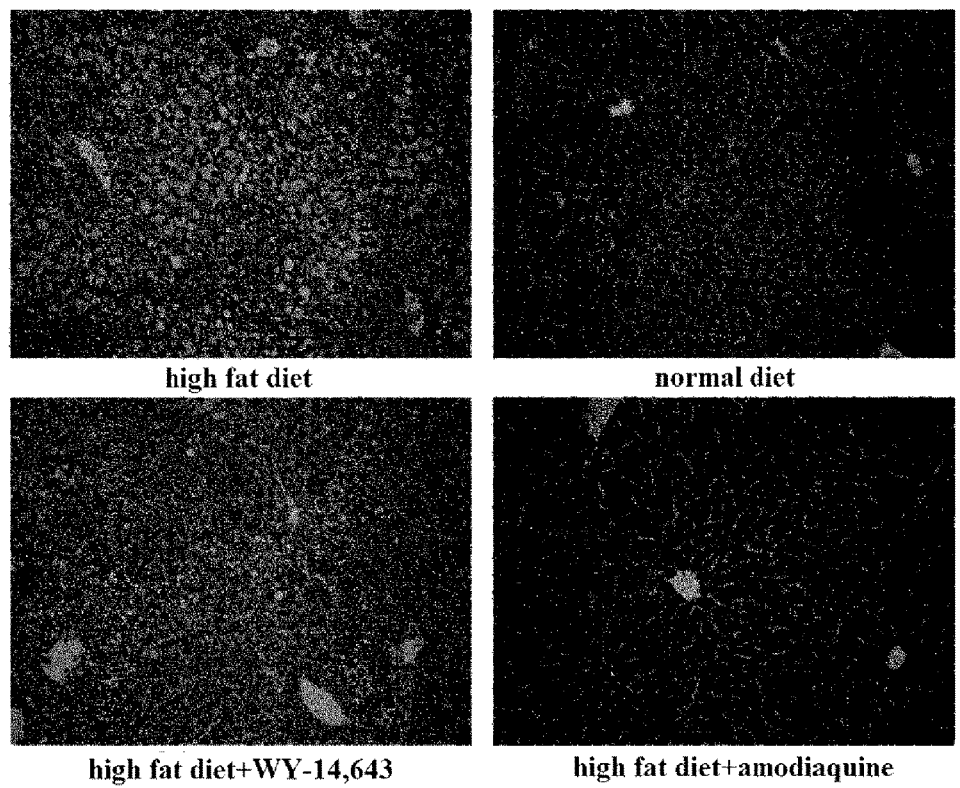
FIG. 8 is a graph showing a histological change in liver cells due to fat accumulation after the liver of an experimental animal fed a high fat diet with amodiaquine for 14 weeks was stained with hematoxylin-eosin.

According to the experiment, as shown in FIG. 8, it can be confirmed that the liver of the high fat-induced obesity mouse was full of fat, but the liver of the high fat-induced obesity mouse treated with amodiaquine may have almost the same appearance as that of a normal mouse.

Therefore, it can be seen from the result that the amodiaquine according to the present invention has an excellent effect of inhibiting fatty liver.

Example 9. Identification of Expression of Target Gene According to PPAR-α Activation in Liver, Muscle and Adipose Tissue by Amodiaquine Administration PPAR-α is known to reduce the synthesis of a fatty acid by inducing expression of ACOX (acyl-CoA oxidase), CPT-1 (carnitine palmitoyl transferase-1), and mCAD (medium chain acyl-CoA dehydrogenase) genes, which are the genes of enzymes involved in the fatty acid oxidation metabolic pathway (Dreyer Christine et al., Cell, 68:879-887, 1992). Therefore, when expression levels of the ACOX, CPT-1 and mCAD genes are measured, a fatty acid oxidation effect may be identified. Therefore, in this example, an effect of the administration of amodiaquine on expression levels of the ACOX, CPT-1 and mCAD genes in the liver, muscle and adipose tissue will be examined.

After mice in the high fat-induced obesity mouse group, which were fed a high fat diet for 14 weeks, among the experimental animals designed in Example 5 were sacrificed by cervical spine dislocation, they were fixed on a dissection stand, and subjected to abdominal dissection with a scalpel to extract the liver, muscle or adipose tissue, and primer sequences for the β-actin, ACOX, CPT-1 and mCAD are as follows:

```
β-actin
forward:
5'-GGG AAG GTG ACA GCA TTG-3' reverse:
5'-ATG AAG TAT TAA GGC GGA AGA TT-3'

ACOX
forward:
5'-ACA CTA ACA TAT CAA CAA GAG GAG-3' reverse:
5'-CAT TGC CAG GAA GAC CAG-3'

CPT-1
forward:
5'-CCA CCT CTT CTG CCT CTA T-3' reverse:
5'-TTC TCA AAG TCA AAC AGT TCC A-3 mCAD
forward:
5'-CCG AAG AGT TGG CGT ATG-3' reverse:
5'-AGC AAG AAT CAC AGG CAT T-3'
```

After each tissue was disrupted using a grinding instrument, RNA was extracted using TRIzol, and cDNA was synthesized using reverse transcription polymerase chain reaction (RT PCR). As a control, β-actin was used, and to determine the expression levels of the ACOX, CPT-1 and mCAD genes, which are target genes according to PPAR-α activation and involved in fatty acid degradation, real-time PCR was performed using primers for each gene (at 95° C. for 3 minutes, 39 cycles of 95° C. for 10 seconds, 60° C. for 10 seconds, 72° C. for 30 seconds, 95° C. for 10 seconds, and 65° C. for 5 seconds). The ACOX, CPT-1 and mCAD calibrated with β-actin, thereby obtaining resultant values. The test results were analyzed to see if there was significance between mice of the high fat-induced obesity mouse control, the amodiaquine-treated mice, and the positive control (WY-14,643)-treated mice according to an independent group t-test, and it was shown that these groups showed a statistically significant difference (*$p<0.05$, $p<0.005$, *$p<0.0005$).

Figure 9A:
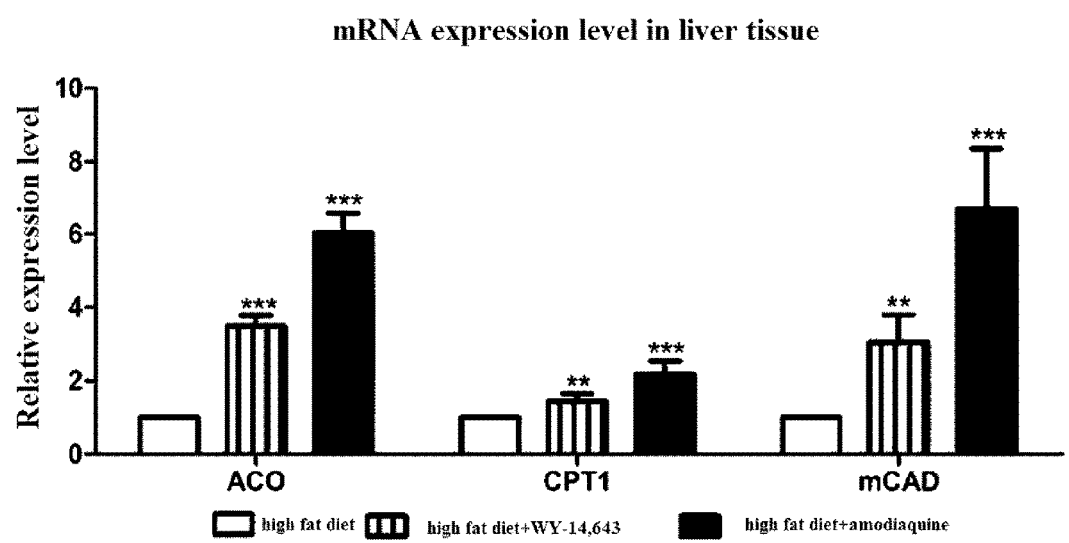
FIG. 9A is a graph showing a result of measuring expression of genes involved in fatty acid oxidation in liver tissue of a high fat-induced obesity mouse fed amodiaquine.
Figure 9B:
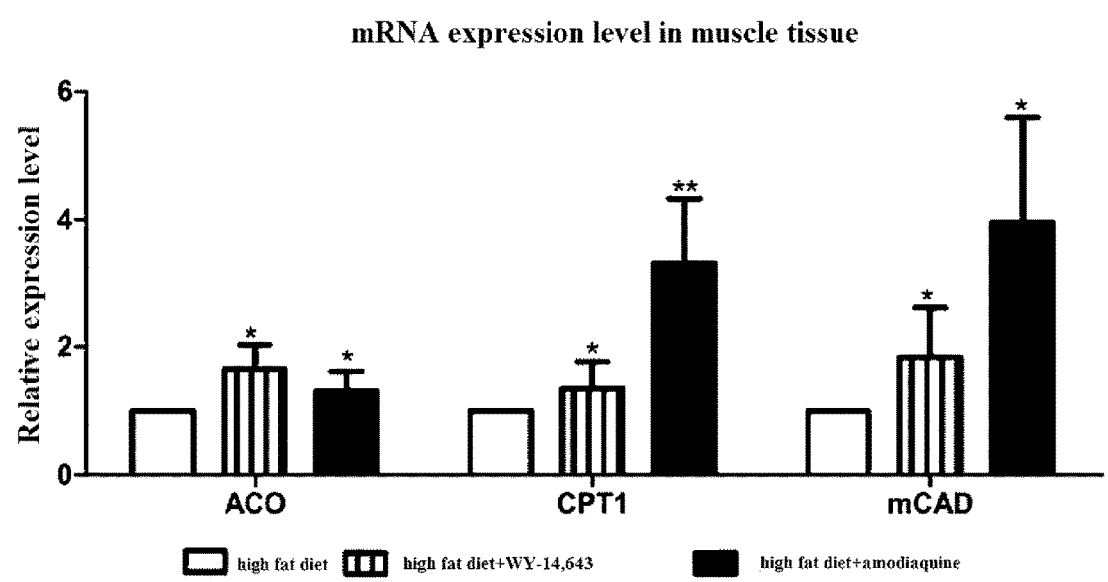
FIGS. 9B and 9C are graphs showing results of measuring expression of genes involved in fatty acid oxidation in muscle tissue (9B) and in adipose tissue (9C), respectively.
Figure 9C:
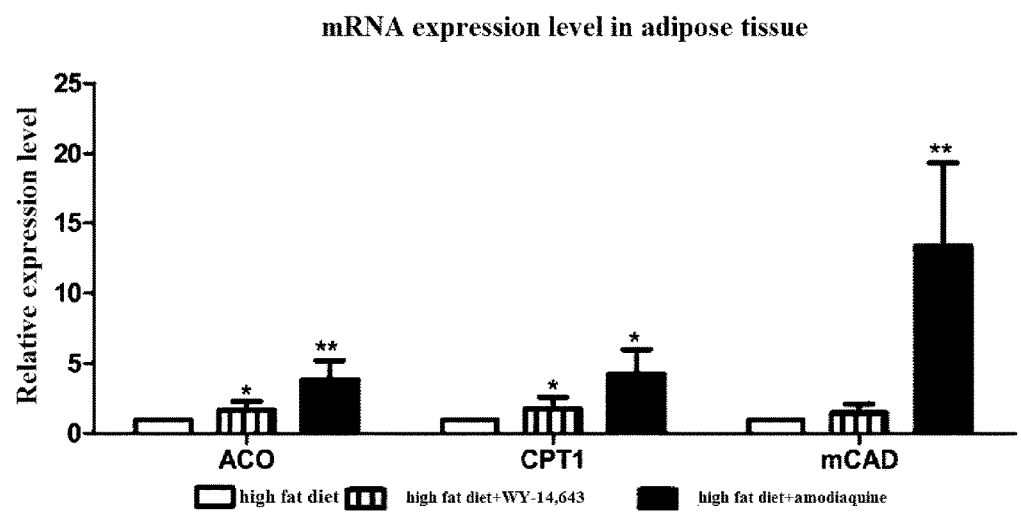

As a result, as shown in FIGS. 9A, 9B and 9C, it was confirmed that the expression levels of the genes were increased almost 2 to 15 times higher in the amodiaquine-treated experimental group, compared to the control.

Therefore, the treatment with amodiaquine increased the expression of ACOX, CPT-1 and mCAD genes, which are target genes according to PPAR-α activation and involved in fatty acid degradation, in each tissue, which means that amodiaquine can regulate the expression of target genes of PPAR-α by activating PPAR-α, and it was determined that oxidation of fatty acids can be promoted, thereby inhibiting fat accumulation.

Example 10. Identification of Expression of Target Genes by Anti-Inflammatory Response in Adipose Tissue According to Administration of Amodiaquine Adipocytes differentiate from mesenchymal stem cells and preadipocytes, and bring about changes in a lipid metabolic function, a saccharometabolic function, and even secretion of adipocytes (Cristina M. Rondinone, Endocrine, 29:81-90, 2006). TNFα, MCP-1 and iNOS increased in obesity patients promote adipose differentiation because of inflammation expression of adipocytes, and increased morbidities of other adult diseases (Tomasz J. Guzik et al., *J Physiol Pharmacol* 57: 505-528, 2006). TNF-α is a cellular secretory substance, which is known to play an important role in inflammatory responses, and MCP-1 is an inflammatory chemokine, which is secreted from adipocytes and known to have an influence on obesity, insulin resistance, and arteriosclerosis. In addition, iNOS is an inflammatory precursor which is known to promote inflammatory responses.

Accordingly, when expression levels of the TNFα, MCP-1 and iNOS genes were measured, an anti-inflammatory effect may be identified. Therefore, in this example, an effect of administration of amodiaquine on the expression levels of the TNFα, MCP-1 and iNOS genes in adipose tissue will be examined.

After mice in the high fat-induced obesity mouse group, which were fed a high fat diet for 14 weeks, among the experimental animals designed in Example 5 were sacrificed by cervical spine dislocation, they were fixed on a dissection stand, and subjected to dissection with a scalpel to extract liver, muscle or adipose tissue, and primer sequences for the β-actin, TNFα, MCP-1 and iNOS are as follows.

```
β-actin
forward:
5'-GGG AAG GTG ACA GCA TTG-3'
```

```
-continued
reverse:
5'-ATG AAG TAT TAA GGC GGA AGA TT-3'

TNFα
forward:
5'-ATG AGA AGT TCC CAA ATG GC-3' reverse:
5'-TTT GAG AAG ATG ATC TGA GTG TGA G-3'

MCP-1
forward:
5'-AAT GAG TAG GCT GGA GAG-3' reverse:
5'-TCT CTT GAG CTT GGT GAC-3' iNOS
forward:
5'-GCT TCT GGC ACT GAG TAA-3' reverse:
5'-GGA GGA GAG GAG AGA GAT-3'
```

After each tissue was disrupted using a grinding instrument, RNA was extracted using TRIzol, and cDNA was synthesized using RT PCR. As a control, β-actin was used, and to determine the expression levels of the TNFα, MCP-1 and iNOS genes involved in inflammation responses, real-time PCR was performed using primers for each gene (at 95° C. for 3 minutes, 39 cycles of 95° C. for 10 seconds, 60° C. for 10 seconds, 72° C. for 30 seconds, 95° C. for 10 seconds, and 65° C. for 5 seconds). The TNFα, MCP-1 and iNOS calibrated with β-actin, thereby obtaining resultant values. The test results were analyzed to see if there was significance between mice of the high fat-induced obesity mouse control, the amodiaquine-treated mice, and the positive control (WY-14,643)-treated mice according to an independent group t-test, and it was shown that these groups showed a statistically significant difference (*$p<0.05$, **$p<0.005$).

Figure 10:
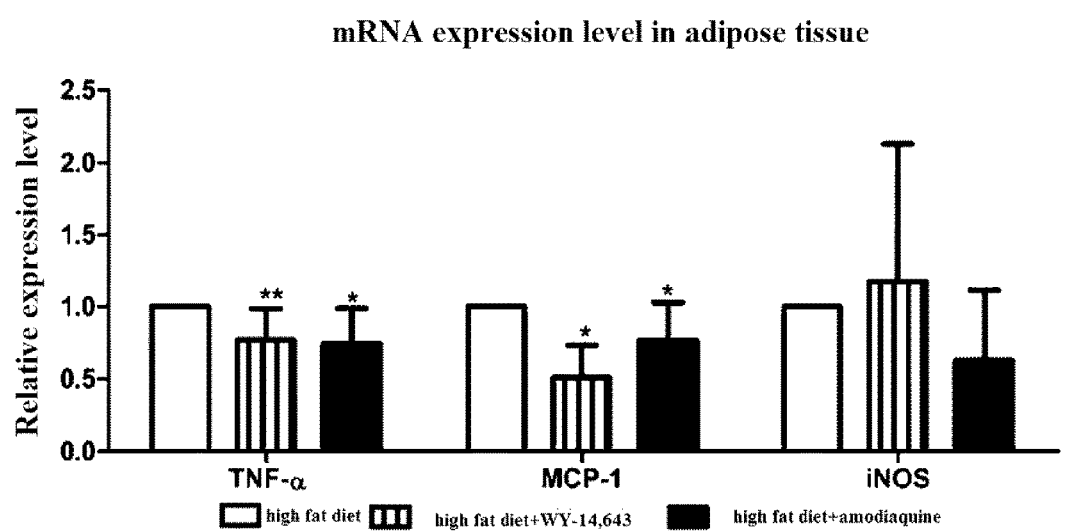
FIG. 10 is a graph showing a result of measuring expression of anti-inflammatory genes in adipose tissue of a high fat-induced obesity mouse fed amodiaquine.

As a result, as shown in FIG. 10, it was confirmed that the expression levels of the genes were decreased almost 5 to 40% in the amodiaquine-treated experimental group, compared to the control.

Therefore, the treatment with amodiaquine inhibited the expression of TNFα, MCP-1 and iNOS genes that are involved in the anti-inflammatory responses in each tissue, and thus it is determined that amodiaquine has an influence on obesity, insulin resistance and arteriosclerosis by inhibiting factors playing an important role in inflammatory responses.

It would be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

The invention claimed is:

1. A method of preventing, alleviating or treating type 2 diabetes responding to peroxisome proliferator-activated receptor-gamma (PPAR-γ) activation and one or more selected from the group consisting of obesity, dyslipidemia, a cardiovascular disease and fatty liver, which respond to peroxisome proliferator-activated receptor-alpha (PPAR-α) activation, the method comprising:

administering, to a subject in need thereof, amodiaquine represented by Formula 1 below or a pharmaceutically acceptable salt thereof as an active ingredient which activates both of PPAR-γ and PPAR-α:

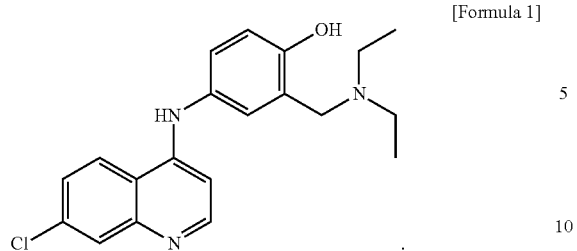
[Formula 1]
2. The method of claim 1, wherein a daily dose of the amodiaquine or the pharmaceutically acceptable salt thereof is 8 mg/kg to 20 mg/kg.
3. The method of claim 1, wherein the dyslipidemia is one or more selected from the group consisting of hyperlipidemia, hypertriglyceridemia, and hypercholesterolemia.
\* \* \* \* \*